United States Patent
Stastka

(10) Patent No.: US 12,220,336 B2
(45) Date of Patent: Feb. 11, 2025

(54) CONSTRAINING MECHANISMS FOR SELECTIVE DEPLOYMENT AND ASSOCIATED METHODS

(71) Applicant: W. L. Gore & Associates, Inc., Newark, DE (US)

(72) Inventor: Jerry J. Stastka, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 877 days.

(21) Appl. No.: 17/282,918

(22) PCT Filed: Oct. 4, 2019

(86) PCT No.: PCT/US2019/054652
§ 371 (c)(1),
(2) Date: Apr. 5, 2021

(87) PCT Pub. No.: WO2020/072876
PCT Pub. Date: Apr. 9, 2020

(65) Prior Publication Data
US 2021/0386567 A1    Dec. 16, 2021

Related U.S. Application Data

(60) Provisional application No. 62/746,270, filed on Oct. 16, 2018, provisional application No. 62/741,948, filed on Oct. 5, 2018.

(51) Int. Cl.
*A61F 2/95* (2013.01)
*A61B 90/00* (2016.01)
*A61B 90/92* (2016.01)

(52) U.S. Cl.
CPC ............. *A61F 2/95* (2013.01); *A61B 90/39* (2016.02); *A61B 90/92* (2016.02); *A61F 2002/9511* (2013.01); *A61F 2250/005* (2013.01); *A61F 2250/0096* (2013.01)

(58) Field of Classification Search
CPC .................................................. A61F 2002/9511
See application file for complete search history.

(56) References Cited

U.S. PATENT DOCUMENTS

| | | |
|---|---|---|
| 4,878,906 A | 11/1989 | Lindemann et al. |
| 5,405,378 A | 4/1995 | Strecker |
| 5,671,790 A | 9/1997 | Andersen et al. |

(Continued)

FOREIGN PATENT DOCUMENTS

| | | |
|---|---|---|
| CA | 2456046 A1 | 12/1999 |
| CN | 103547235 A | 1/2014 |

(Continued)

OTHER PUBLICATIONS

"About Denier" https://standardfiber.com/about-denier (Year: 2012).

(Continued)

*Primary Examiner* — Melanie R Tyson
*Assistant Examiner* — Yasniary De La Caridad Morales

(57) ABSTRACT

Various aspects of the present disclosure are directed toward medical device deployment apparatuses, systems, and methods that include a constraint configured to releasably constrain the medical device. The constraint may be unraveled at different rates.

24 Claims, 8 Drawing Sheets

(56) References Cited

U.S. PATENT DOCUMENTS

| | | |
|---|---|---|
| 6,224,627 B1 | 5/2001 | Armstrong et al. |
| 6,302,891 B1 | 10/2001 | Nadal |
| 6,315,792 B1 | 11/2001 | Armstrong et al. |
| 6,352,553 B1 | 3/2002 | Van et al. |
| 9,375,215 B2 | 6/2016 | Cully et al. |
| 9,427,307 B2 | 8/2016 | Pearson et al. |
| 9,439,791 B2 | 9/2016 | Vong et al. |
| 9,622,893 B2 | 4/2017 | Huser |
| 9,717,612 B2 | 8/2017 | Dorn et al. |
| 2002/0045930 A1 | 4/2002 | Burg et al. |
| 2004/0122503 A1 | 6/2004 | Campbell et al. |
| 2007/0038310 A1 | 2/2007 | Guetty |
| 2008/0255580 A1 | 10/2008 | Hoffman et al. |
| 2009/0326640 A1 | 12/2009 | Yoshimura et al. |
| 2010/0011976 A1 | 1/2010 | Armstrong et al. |
| 2011/0218613 A1 | 9/2011 | Leopold et al. |
| 2012/0130475 A1 | 5/2012 | Shaw |
| 2012/0259406 A1 | 10/2012 | Schreck et al. |
| 2013/0123900 A1 | 5/2013 | Eblacas et al. |
| 2013/0245745 A1 | 9/2013 | Vong et al. |
| 2014/0148895 A1 | 5/2014 | King |
| 2014/0180378 A1 | 6/2014 | Roeder |
| 2014/0200649 A1 | 7/2014 | Essinger et al. |
| 2014/0277363 A1 | 9/2014 | Armstrong et al. |
| 2015/0081000 A1 | 3/2015 | Hossainy et al. |
| 2015/0082595 A1 | 3/2015 | King |
| 2015/0173753 A1* | 6/2015 | Spivey ............ A61B 17/06166 606/228 |
| 2015/0250630 A1 | 9/2015 | Irwin et al. |
| 2016/0199207 A1 | 7/2016 | Treacy et al. |
| 2017/0151079 A1 | 6/2017 | Shaw |
| 2017/0189212 A1 | 7/2017 | Eller et al. |
| 2017/0348099 A1 | 12/2017 | Mendelson et al. |
| 2018/0280171 A1 | 10/2018 | Gloss et al. |
| 2021/0386569 A1 | 12/2021 | Stastka |
| 2022/0031485 A1 | 2/2022 | Ramirez et al. |
| 2022/0211528 A1 | 7/2022 | Gore et al. |
| 2022/0211529 A1 | 7/2022 | Skelton |
| 2022/0296399 A1 | 9/2022 | Gore et al. |
| 2023/0099043 A1 | 3/2023 | Gore et al. |
| 2023/0225891 A1 | 7/2023 | Stastka |

FOREIGN PATENT DOCUMENTS

| | | | |
|---|---|---|---|
| CN | 105530895 A | 4/2016 | |
| CN | 106102596 A | 11/2016 | |
| EP | 0950385 A2 | 10/1999 | |
| EP | 1087726 A1 | 4/2001 | |
| EP | 1087726 B1 * | 5/2004 | ............ A61F 2/82 |
| EP | 2298248 A1 | 3/2011 | |
| EP | 2735283 A1 | 5/2014 | |
| EP | 2749251 B1 | 7/2016 | |
| JP | 06-503734 A | 4/1994 | |
| JP | 2000-503359 A | 3/2000 | |
| JP | 2000-503559 A | 3/2000 | |
| JP | 2002-518086 A | 6/2002 | |
| JP | 2003-052833 A | 2/2003 | |
| JP | 2005-270432 A | 10/2005 | |
| JP | 2005-304792 A | 11/2005 | |
| JP | 2006-510453 A | 3/2006 | |
| JP | 2009-523565 A | 6/2009 | |
| JP | 2018-501902 A | 1/2018 | |
| JP | 2021-566524 A | 7/2022 | |
| WO | 97/21402 A1 | 6/1997 | |
| WO | 99/65420 A1 | 12/1999 | |
| WO | 2007/084762 A2 | 7/2007 | |
| WO | 2009/140861 A1 | 11/2009 | |
| WO | 2016/115007 A1 | 7/2016 | |
| WO | 2019/075069 A1 | 4/2019 | |
| WO | 2019/240799 A1 | 12/2019 | |
| WO | 2019/240800 A1 | 12/2019 | |
| WO | 2020/068957 A1 | 4/2020 | |
| WO | 2020/231387 A1 | 11/2020 | |
| WO | 2021/173648 A1 | 9/2021 | |

OTHER PUBLICATIONS

"What is Denier" https://www.onlinefabricstore.com/makersmill/what-is-denier/ (Year: 2012).

Merriam-Wester online dictionary, "knit" definition, accessed on Aug. 24, 2023, https://www.merriam-webster.com/dictionary/knit (Year: 2023) (Year: 2023).

International Preliminary Report on Patentability received for PCT Patent Application No. PCT/US2019/031761, mailed on Nov. 25, 2021, 9 pages.

International Preliminary Report on Patentability received for PCT Patent Application No. PCT/US2019/031769, mailed on Nov. 25, 2021, 10 pages.

International Preliminary Report on Patentability received for PCT Patent Application No. PCT/US2019/031780, mailed on Nov. 25, 2021, 7 pages.

International Preliminary Report on Patentability received for PCT Patent Application No. PCT/US2019/052921, mailed on Apr. 8, 2021, 8 pages.

International Preliminary Report on Patentability received for PCT Patent Application No. PCT/US2019/054630, mailed on Apr. 15, 2021, 9 pages.

International Preliminary Report on Patentability received for PCT Patent Application No. PCT/US2019/054652, mailed on Apr. 15, 2021, 8 pages.

International Search Report and Written Opinion received for PCT Patent Application No. PCT/US2019/031761, mailed on Jan. 22, 2020, 11 pages.

International Search Report and Written Opinion received for PCT Patent Application No. PCT/US2019/031769, mailed on Jan. 23, 2020, 16 pages.

International Search Report and Written Opinion received for PCT Patent Application No. PCT/US2019/031780, mailed on Jan. 20, 2020, 8 pages.

International Search Report and Written Opinion received for PCT Patent Application No. PCT/US2019/052921, mailed on Jan. 29, 2020, 13 pages.

International Search Report and Written Opinion received for PCT Patent Application No. PCT/US2019/054630, mailed on Jan. 29, 2020, 11 pages.

International Search Report and Written Opinion received for PCT Patent Application No. PCT/US2019/054652, mailed on Jan. 29, 2020, 9 pages.

International Search Report and Written Opinion received for PCT Patent Application No. PCT/US21/19386, mailed on Jun. 18, 2021, 12 pages.

International Search Report and Written Opinion received for PCT Patent Application No. PCT/US21/25919, mailed on Dec. 23, 2021, 20 pages.

International Preliminary Report on Patentability received for PCT Patent Application No. PCT/US2021/037311, mailed on Dec. 29, 2022, 8 pages.

International Search Report and Written Opinion received for PCT Patent Application No. PCT/US2021/037311, mailed on Sep. 30, 2021, 12 pages.

Dictionary Definition of "Knot" Dictionary.com, https://www.dictionary.com/browse/knot. (Year: 2024).

* cited by examiner

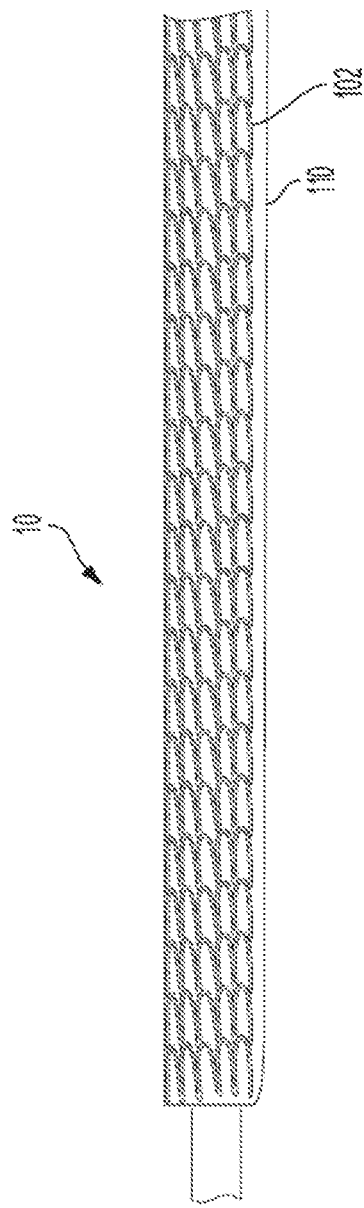
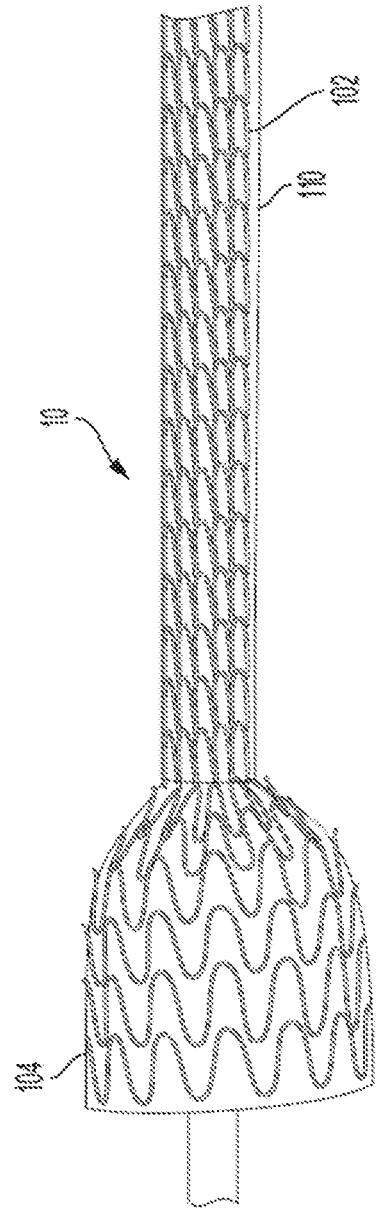

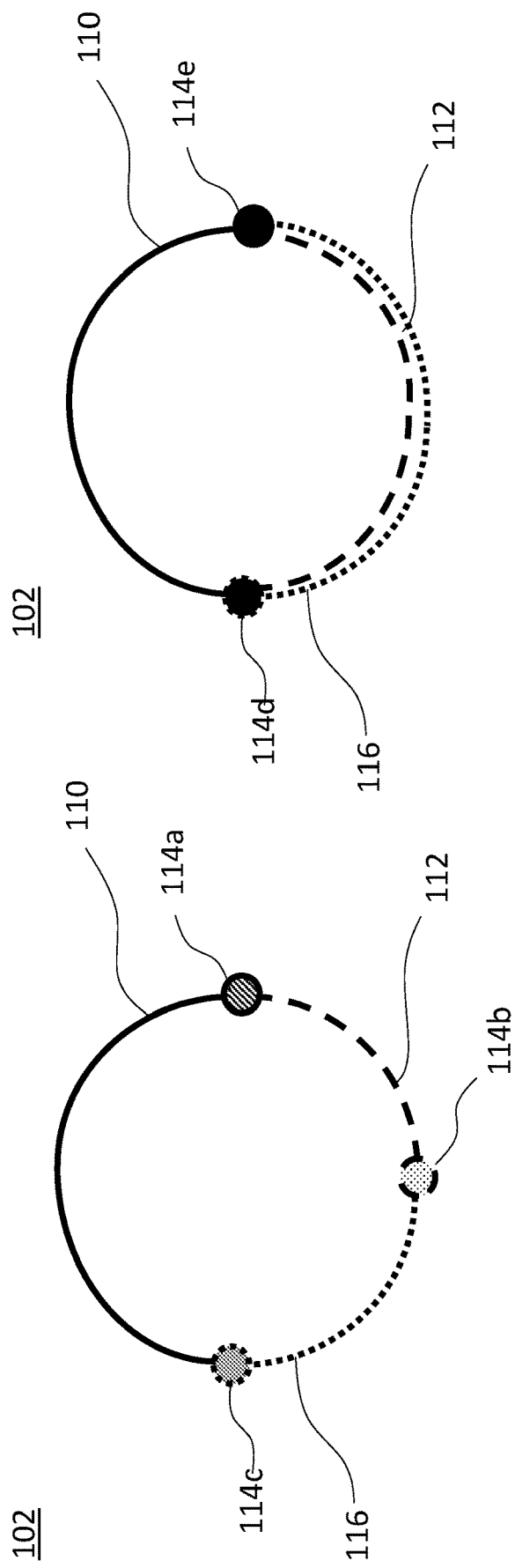

CONSTRAINING MECHANISMS FOR SELECTIVE DEPLOYMENT AND ASSOCIATED METHODS

CROSS-REFERENCE TO RELATED APPLICATION

This application is a national phase application of PCT Application No. PCT/US2019/054652, internationally filed on Oct. 4, 2019, which claims the benefit of Provisional Application No. 62/746,270, filed Oct. 16, 2018, and also claims the benefit of Provisional Application No. 62/741,948, filed Oct. 5, 2018, all of which are incorporated herein by reference in their entireties for all purposes.

FIELD

The present disclosure relates to apparatuses, systems, and methods that include constraints used in delivery of implantable medical devices. More specifically, the present disclosure relates to apparatuses, systems, and methods that include constraints for selective deployment of an expandable device during device delivery.

BACKGROUND

Stents and stent-grafts may be utilized to radially support a variety of tubular passages in the body, including arteries, veins, airways, gastrointestinal tracts, and biliary tracts. The preferred method of placing these devices has been to use specialized delivery systems to precisely place and deploy a device at the site to be treated. These delivery systems allow the practitioner to minimize the trauma and technical difficulties associated with device placements. Attributes of delivery systems include: low profile; ability to pass through introducer sheaths; ability to negotiate tortuous vasculature, smoothly and atraumatically; protection of constrained devices; and ability to accurately position and deploy the device.

Stents or stent-grafts may be deployed and plastically deformed by using an inflatable balloon (e.g., balloon expandable stents) or to self-expand and elastically recover (e.g., "self expandable" devices) from a collapsed or constrained delivery diameter to an expanded and deployed diameter. Some stents are designed to elastically recover by being manufactured at their functional diameter out of a material that has elastic recovery properties, and then radially compressed to be mounted on a delivery catheter.

These stent and stent-graft devices may be held, compressed, or constrained in the delivery configuration prior to and during delivery to a target location.

SUMMARY

In one example ("Example 1"), a medical device deployment apparatus includes a constraint configured to releasably constrain the medical device and including a plurality of interlocking strands forming a first knot row configured to unravel at a first deployment rate and a second knot row configured to unravel at a second deployment rate that is different from the first deployment rate and wherein disrupting a strand of the first knot row initiates unraveling of at least a portion of the constraint at the first deployment rate, and disrupting a strand of the second knot row initiates unravelling of at least a portion of the constraint at the second deployment rate.

In another example ("Example 2"), further to the apparatus of Example 1, a deployment ratio between the first knot row and the second knot row is 10:1.

In another example ("Example 3"), further to the apparatus of any one of Examples 1-2, the deployment apparatus also includes a third knot row spaced from the first and second knot rows, wherein disrupting a strand of the third knot row initiates unraveling of at least a portion of the constraint at a third deployment rate that is different than the first and second deployment rates.

In another example ("Example 4"), further to the apparatus of Example 3, a deployment ratio between the first knot row and the second knot row is different than the deployment ratio between the second knot row and the third knot row.

In another example ("Example 5"), further to the apparatus of Example 4, the first, second, and third knot rows are evenly spaced about a circumference of the constraint.

In another example ("Example 6"), further to the apparatus of Example 4, the first, second, and third knot rows are unevenly spaced about the circumference of the constraint.

In another example ("Example 7"), further to the apparatus of Examples 1-6, disrupting the first knot row includes breaking a strand of the first knot row, and wherein disrupting the second knot row includes breaking a strand of the second knot row.

In another example ("Example 8"), further to the apparatus of Examples 1-7, disrupting the first knot row includes altering tension of at least one strand of the first knot row, and wherein disrupting the second knot row includes altering tension of at least one strand of the second knot row.

In another example ("Example 9"), further to the apparatus of Examples 1-8, the first knot row is configured to disrupt before the second knot row.

In another example ("Example 10"), further to the apparatus of Examples 1-9, the second deployment rate is faster than the first deployment rate.

In another example ("Example 11"), further to the apparatus of Examples 1-10, the strands of the first knot row are distinguishable from the strands of the second knot row by color.

In another example ("Example 12"), further to the apparatus of Examples 1-11, the strands of the first knot row are distinguishable from the strands of the second knot row by marking.

In another example ("Example 13"), further to the apparatus of Examples 1-12, the strands of the first knot row are distinguishable from the strands of the second knot row by texture In another example ("Example 14"), further to the apparatus of Examples 1-13, the plurality of interlocking strands forms a warp knit pattern.

In another example ("Example 15"), further to the apparatus of any one of Examples 1-14, a pattern formed by the plurality of interlocking strands differs along a length of the constraint.

In another example ("Example 16"), further to the apparatus of Example 15, the plurality of interlocking strands form a plurality of knot rows, including the first knot row and the second knot row, that increases or decreases in number along the length of the constraint.

In another example ("Example 17"), further to the apparatus of Example 15, the plurality of interlocking strands form a plurality of knot rows, including the first knot row and the second knot row, and interactions between the plurality of interlocking strands differs along the length of the constraint.

In one example ("Example 18"), a method of using a medical device deployment apparatus includes providing a constraint including a first knot row and a second knot row; disrupting a strand of the first knot row to initiate unravelling of at least a portion of the constraint at a first deployment rate; and disrupting a strand of the second knot row to initiate unravelling of at least a portion of the constraint at a second deployment rate that is greater than the first deployment rate.

In another example ("Example 19"), further to the method of Example 18, the method also includes disrupting a strand of a third knot row to unravel at least a portion of the constraint at a third deployment rate that is different from the first and second deployment rates.

In another example ("Example 20"), further to the method of any one of Examples 18-19, disrupting the strand of the first knot row includes breaking the strand.

In one example ("Example 21"), a medical device deployment includes a removable constraint having a circumference comprising multiple interlocking strands in the form of a warp knit having multiple knot rows spaced around the circumference; wherein when one of the knot rows is disrupted, the removable constraint will unravel and be remotely removable when a force is applied to a deployment line and wherein the multiple knot rows are unevenly distributed around the circumference and the rate of removable constraint removal is different depending upon which of the knot rows is disrupted.

In another example ("Example 22"), further to the apparatus of Example 21, the multiple knot rows are configured disrupt in response to a user selection of one of the multiple rows to allow the user to select a rate of constraint removal.

In another example ("Example 23"), further to the apparatus of any one of Examples 20-21, the multiple rows are configured to unravel in a set order to define a rate of constraint removal.

In another example ("Example 24"), further to the apparatus of any one of Examples 20-21, the interlocking strands are distinguishable from one another.

In another example ("Example 25"), further to the apparatus of Example 24, the interlocking strands are distinguishable from one another by coloring.

In another example ("Example 26"), further to the apparatus of Example 24, the interlocking strands are distinguishable from one another by marking.

In another example ("Example 27"), further to the apparatus of Example 24, the interlocking strands are distinguishable from one another by texture.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

FIG. 6A is an image of a delivery system in a delivery configuration, in accordance with an embodiment;

FIG. 6B is an image of the delivery system, shown in FIG. 6A, in a semi-deployed configuration, in accordance with an embodiment.

FIG. 8A is an end view of a constraint having an example first knot row pattern, in accordance with an embodiment.

FIG. 8B is an end view of the constraint, shown in FIG. 8A, having an example second knot row pattern, in accordance with an embodiment As the terms are used herein with respect to ranges of measurements "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error, differences in measurement and/or manufacturing equipment calibration, human error in reading and/or setting measurements, adjustments made to optimize performance and/or structural parameters in view of differences in measurements associated with other components, particular implementation scenarios, imprecise adjustment and/or manipulation of objects by a person or machine, and/or the like.

Figure 1:
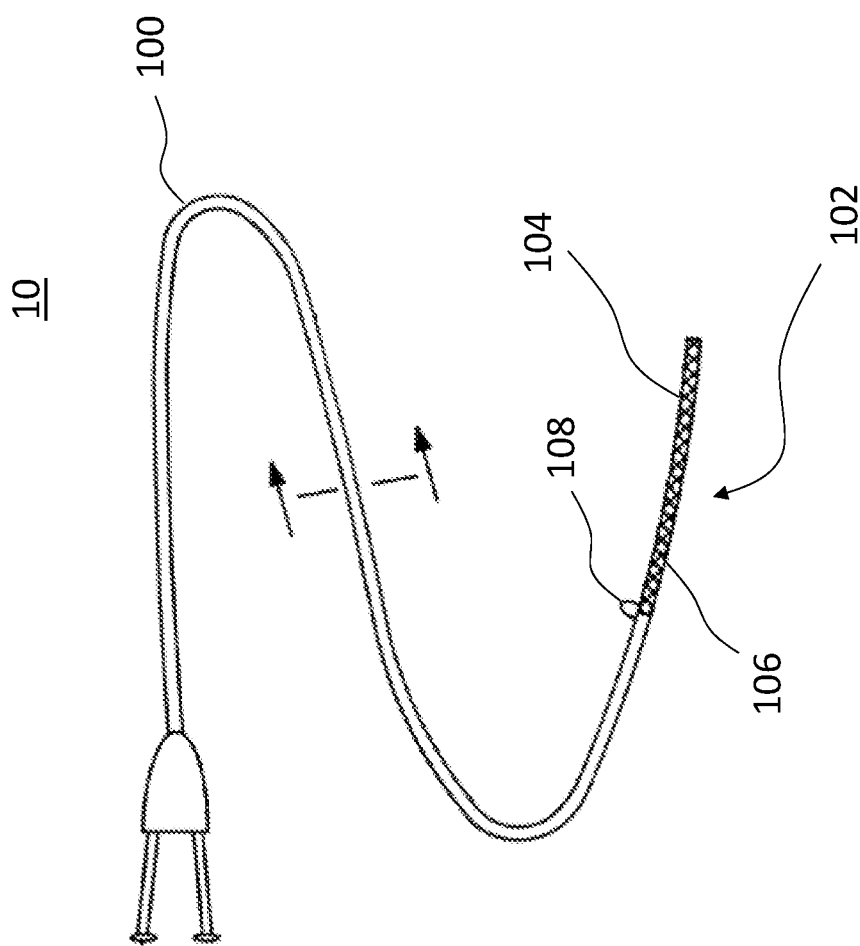
FIG. 1 is a top plan view of a delivery system including a catheter with a constraint, in accordance with an embodiment.

The foregoing Examples are just that, and should not be read to limit or otherwise narrow the scope of any of the inventive concepts otherwise provided by the instant disclosure. While multiple examples are disclosed, still other embodiments will become apparent to those skilled in the art from the following detailed description, which shows and describes illustrative examples. Accordingly, the drawings and detailed description are to be regarded as illustrative in nature rather than restrictive in nature.

DETAILED DESCRIPTION

Persons skilled in the art will readily appreciate that various aspects of the present disclosure can be realized by any number of methods and apparatus configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

Various aspects of the present disclosure are directed toward apparatuses, systems, and methods that include forming or manufacturing a constraint. The constraining mechanisms are configured to hold, compress, or constrain an implantable medical device (e.g., a stent, stent-graft, balloon, filter, or other expandable medical device) in a delivery configuration prior to and during delivery to a target location. In certain instances, the constraint includes one or more fibers. In certain instances, the constraint disclosed herein allows for altering of deployment characteristics of the implantable medical device prior to or during deployment of the device. Thus, the deployment system is adaptable to varying situations that may arise during a procedure.

FIG. 1 is a top plan view of a catheter 100 with a constraint 102, according to some embodiments. As shown in FIG. 1, the constraint 102 is configured to constrain an implantable medical device 104 to a delivery configuration. The constraint 102 may include one or more fibers 106 arranged about the implantable medical device 104 to maintain the constraint 102 in a constrained configuration.

The constraint 102 is arranged along a length of the implantable medical device 104. The constraint 102 is also circumferentially arranged about the implantable medical device 104 and may substantially cover the implantable medical device 104 for delivery. The one or more fibers 106 may be arranged within a lumen (not shown) of the catheter 100 and extend toward a proximal end of the catheter 100 that is arranged external to a patient during delivery of the implantable medical device 104. The one or more fibers 106 include a proximal end 108 that a user may apply tension to in order to release the constraint 102 and deploy the implantable medical device 104.

In certain instances, the one or more fibers 106 release similar to a rip cord such that interlocking portions (e.g., overlapping fibers or knots) sequentially release along the length of the implantable medical device 104. As is explained in greater detail below, the constraint 102 is formed by interlocking together the one or more fibers 106 directly on the implantable medical device 104. As compared to prior multiple fiber constraints which are knitted together and then subsequently arranged about a constrained device, the constraint 102 is formed directly on the implantable medical device 104. The expandable medical device 104 may be a stent, stent-graft, a balloon, or a similar device.

Figure 2:
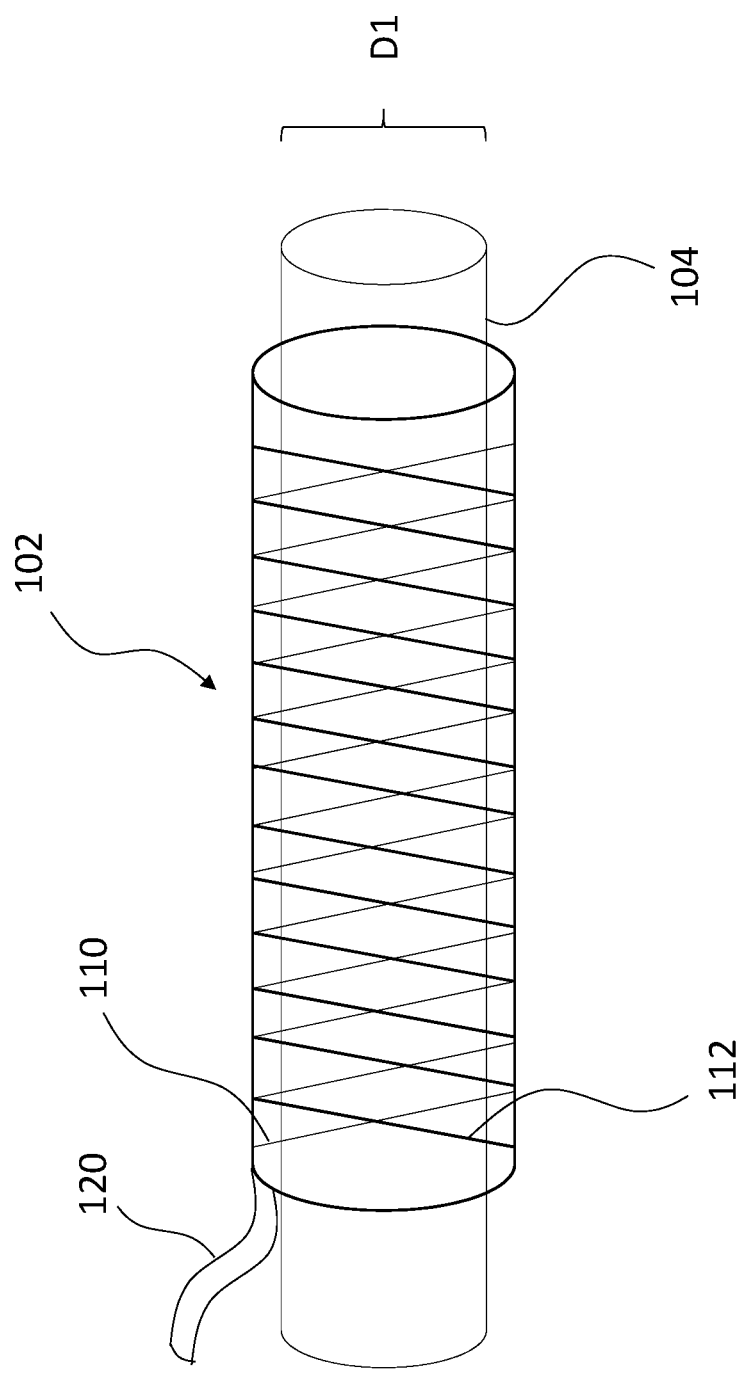
FIG. 2 is a side view of an implantable medical device including a constraint, in accordance with an embodiment.

FIG. 2 is a side view of the device 104 including the constraint 102, in accordance with an embodiment. As shown, the device 104 includes a delivery diameter D1 and a deployed diameter D2 (not shown) that is larger than the delivery diameter D1. The removable constraint 102 is attached to the device 104 at its delivery diameter D1. As shown, the constraint 102 includes at least two interlocking strands in the form of a warp knit. For example, the constraint 102 may include a first interlocking strand 110 and a second interlocking strand 112. The first and/or the second interlocking strand(s) 110, 112 may operate, for example, as a deployment line 120 configured to release the constraint 102 and transition the device 104 from the delivery diameter D1 to the deployed diameter D2 in response to a force applied to the deployment line 120 (which may be coupled to one or more of the knot rows 114 as discussed in further detail below).

The device 104 may have a desired deployed diameter D2 from about 5 mm-15 mm, or 6 mm-9 mm, or 6 mm-12 mm, for example, and a delivery diameter D1 that is less than the deployed diameter D2. For example, in some instances, a ratio of the delivery diameter D1 of the device 104 to the deployed diameter D2 (not shown) of the device 104 is less than about 0.3, less than about 0.29, less than about 0.28, less than about 0.27, or less than about 0.26. For reference, the term "diameter" is not meant to require a circular cross-section, and is instead to be understood broadly to reference a maximum transverse cross-sectional dimension of a device 104.

Figure 3:
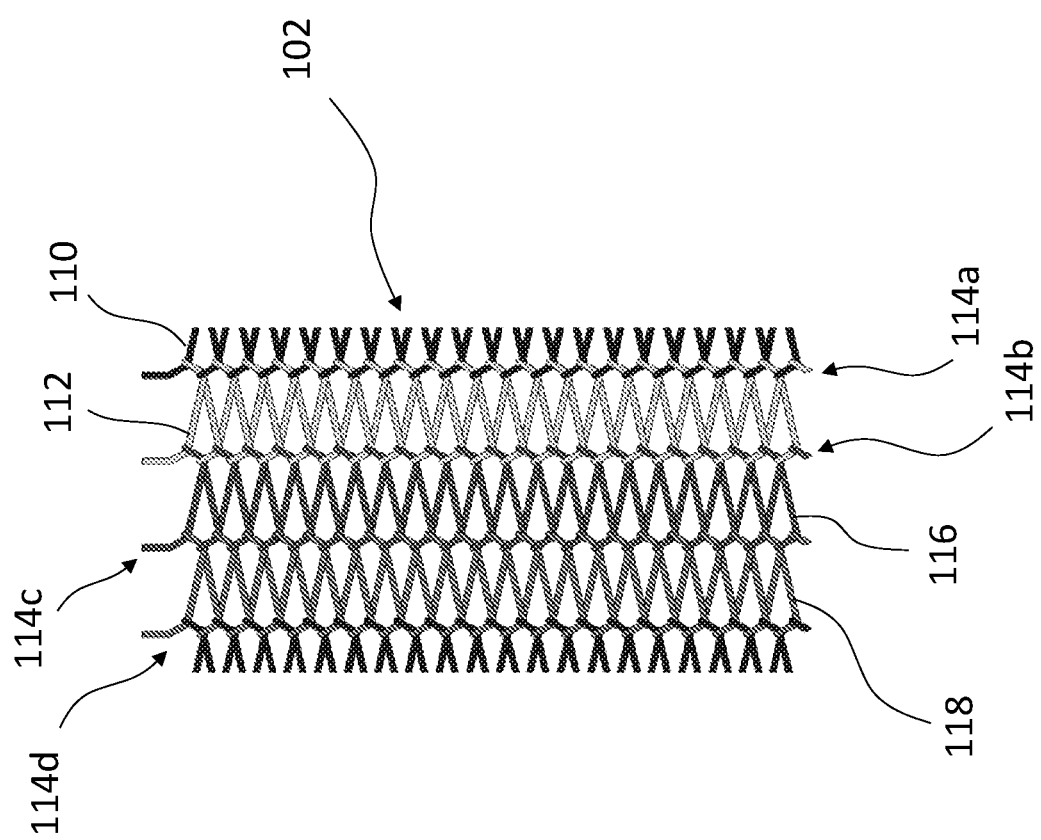
FIG. 3 is a schematic view of interwoven strands, in accordance with an embodiment.

FIG. 3 is a schematic view of interwoven strands, in accordance with an embodiment. As shown, the interlocking strands are interwoven with one another in the warp knit pattern to form knot rows 114 (e.g., the first interlocking strand 110 is interwoven with the second interlocking strand 112 to form a first knot row 114a, and so on). As shown, in some instances, the constraint 102 may include more than two interlocking strands. For example, the constraint 102 may also include a third interlocking strand 116 and a fourth interlocking strand 118. Similar to the first wo interlocking strands 110, 122, the second interlocking strand 112 can be interwoven with the third interlocking strand 116 to form a second knot row 114b, and subsequently, the third interlocking strand 116 can be interwoven with the fourth interlocking strand 118 to form a third knot row 114c. Additional rows 114 may be similarly formed with additional interlocking strands. Though the constraint 102 is described above with reference to two, three, and four interlocking strands and corresponding knot rows, the constraint 102 can have any number of interlocking strands and knot rows as desired. For example, the constraint 102 can include three, five, six, seven, eight, or more interlocking strands and respective knot rows 114.

In various instances, the knot rows 114 are configured to deploy or unravel at different deployment rates. In certain instances, the knot rows 114 are configured to deploy or unravel at different deployment rates due to the positioning of the knot rows about the circumference of the constraint 102. The deployment ratio may be the deployment rate of one knot row 114 compared to the deployment rate of another knot row 114.

Figure 4:
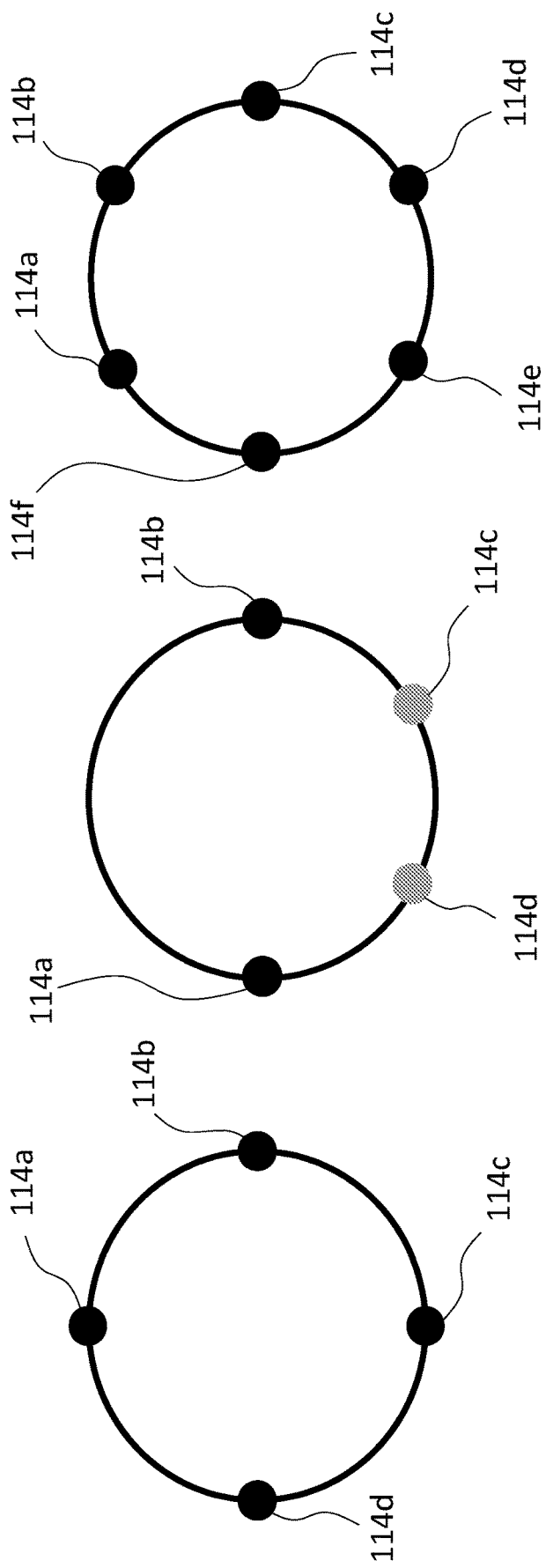
FIGS. 4A-4C are end views of a constraint showing example knot row positioning, in accordance with an embodiment.

FIGS. 4A-4C are end views of the constraint 102 showing example knot row 114 positioning, in accordance with an embodiment. The knot rows 114 can be spaced around the circumference of the constraint 102 any amount as desired. For example, the knot rows 114 may be spaced evenly around the circumference of the constraint 102 or unevenly around the circumference of the constraint 102.

As shown in FIG. 4A, in some instances, the knot rows 114 can be spaced approximately 90 degrees apart from one another. For example, in instances where there are four knot rows (e.g., first through fourth knot rows 114a-d), each of the knot rows 114a-d may be spaced 90 degrees apart. For example, the first knot row 114a is spaced 90 degrees from the second knot row 114b, which is spaced 90 degrees from the third knot row 114c with each of the knot rows 114a-d being spaced 90 degrees apart. In these instances, the deployment ratio of each knot row to an adjacent knot row is approximately 15:1 (e.g., the deployment ratio of the first knot row 114a to the second knot row 114b is approximately 15:1, the deployment ratio of the second knot row 114b to the third knot row 114c is approximately 15:1).

FIG. 4B shows a constraint 102 having unevenly spaced knot rows 114 with varying deployment ratios. As shown, the first and second knot rows 114a, 114b can be spaced approximately 180 degrees apart from one another along the circumference of the constraint 102. The second and third knot rows 114b, 114c and the third and fourth knot rows 114c, 114d can be spaced approximately 60 degrees apart from one another. Thus, the deployment ratio between the second and third knot rows 114b, 114c and the third and fourth knot rows 114c, 114d is approximately 10:1. In these instances, the deployment ratio of the first knot row 114a to the second knot row 114b is greater than the deployment ratio of the second knot row 114b to the third knot row 114c and the third knot row 114c to the fourth knot row 114d. Thus, the first and second knot rows 114a, 114b will deploy slower, while the remaining knot rows (e.g., third and fourth knot rows 114c, 114d) will deploy faster.

In certain instances, the constraint 102 may have less than five knot rows 114, as shown that are unevenly spaced apart from one another along the circumference of the constraint 102. For example, the constraint 102 may have three knot rows 114 (e.g., as shown in FIG. 8A), seven knot rows 114, nine knot rows 144 or another odd number of rows that are unevenly spaced apart from one another along the circumference of the constraint 102. As noted above, deployment ratio of the constraint 102 may be changed based on a user disrupting of a strand of a particular knot row 114, which may have different deployment ratios.

FIG. 4C shows a constraint 102 having six knot rows 114 (e.g., first knot row 114a, second knot row 114b, third knot row 114c, fourth knot row 114d, fifth knot row 114e, and sixth knot row 114f) spaced evenly about the circumference of the constraint 102. The knot rows 114 are spaced approximately 60 degrees apart from one another. For example, the first knot row 114a is spaced about 60 degrees from the second knot row 114b, the second knot row 114b is spaced about 60 degrees from the third knot row 114c, and so on. In these instances, the knot rows 114 have a deployment ratio of approximately 10:1. In other terms, the ratio of the deployment rate of the first knot row 114a to the deployment rate of the second knot row 114b is about 10:1, the ratio of the deployment rate of the second knot row 114b to the third knot row 114c is about 10:1.

In various instances, disrupting of a strand of the first knot row 114a initiates unraveling of at least a portion of the constraint 102 at a first deployment rate that is associated with the first knot row 114a. Disrupting of a strand of the second knot row 114b initiates unraveling of at least a portion of the constraint 102 at a second deployment rate that is associated with the second knot row 114b. The first deployment rate and the second deployment rate of the first and second knot rows 114a, 114b, respectively, may be the same or different depending on the positioning of the knot rows 114 about the circumference of the constraint 102 and their respective deployment ratios. For example, the first deployment rate may be faster than the second deployment rate, while in other instances, the second deployment rate is faster than the first deployment rate.

In various instances, disrupting of a strand of the knot rows 114 to initiate unravel of the knot rows 114 can include breaking the strand, applying a force to the strand, or altering tension on the strand. In certain instances, the first knot row 114a may be configured to disrupt and unravel before the second knot row 114b and/or any number of subsequent knot rows 114.

Figure 5:
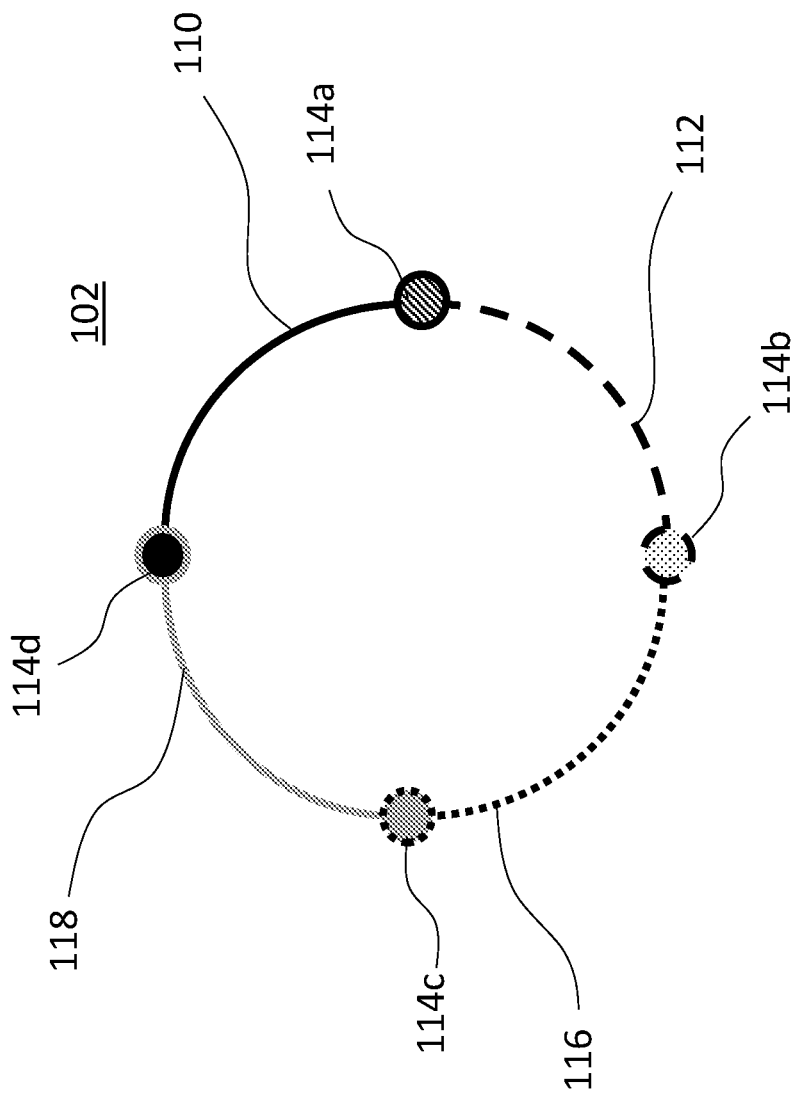
FIG. 5 is an end view of a constraint showing example knot row positioning, in accordance with an embodiment.

FIG. 5 is an end view of the constraint 102 showing example knot row 114 deployment, in accordance with an embodiment. In some instances, each respective interlocking strand and knot row are configured to unravel selectively by the user. For example, as shown, when one of the interlocking strands (e.g., the first interlocking strand 110, for example) of the first knot row 114a is disrupted, the first knot row 114a unravels at the first deployment rate and a portion of the constraint 102 is released. After initiating unravel of the first knot row 114a, one of the interlocking strands of the second knot row 114b (e.g., the second interlocking strand 112, for example) may be disrupted by the user, thus initiating unravel of the second knot row 114b at the second deployment rate and release of another portion of the constraint 102. After initiating unravel of the second knot row 114b, one of the interlocking strands of the third knot row 114c (e.g., the third interlocking strand 116, for example) may be disrupted by the user, thus initiating unravel of the third knot row 114c at the third deployment rate and release of another portion of the constraint 102. After initiating unravel of the third knot row 114c, one of the interlocking strands of the fourth knot row (e.g., the fourth interlocking strand 118, for example) may be disrupted by the user, thus initiating unravel of the fourth knot row 114d at a fourth deployment rate and release of another portion of the constraint 102. This release method can continue for consecutive knot rows until the constraint 102 is fully released. In other instances, disrupting of one of the rows 114 may independently release the constraint 102 and the user may alter the deployment ratio based on the selection of the knot rows 114.

In various instances, the user can actively select which knot row 114 to deploy at certain times. For example, the knot rows 114 do not have to be deployed consecutively around the circumference of the device 104. For example, the first knot row 114a could be deployed first, followed by the third or fourth knot rows 114c, 114d. Since each of the knot rows 114 can have a different deployment characteristic (e.g., deployment rate, deployment ratio), the user can deliberately deploy knot rows 114 that will provide the deployment characteristics desired during a procedure.

In some instances, the interlocking strands of the first knot row 114a may be distinguishable from the interlocking strands of the second knot row 114b. For example, the interlocking strands of the first and second knot rows 114a, 114b may have differing strand characteristics such as color, markings, and/or texture. For example, one of the first and second knot rows 114a, 114b may include a first color and the other of the first and second knot rows 114a, 114b may include a second color. The different colors of the first and second knot rows 114a, 114b indicate to a user that the first and second knot rows 114a, 114b have different rates of deployment. In addition, one of the first and second knot rows 114a, 114b may include a first mark (e.g., visual indicator) and the other of the first and second knot rows 114a, 114b may include a second mark. The different markings of the first and second knot rows 114a, 114b indicate to a user that the first and second knot rows 114a, 114b have different rates of deployment. In other instances, one of the first and second knot rows 114a, 114b may include a first texture and the other of the first and second knot rows 114a, 114b may include a second texture. The different texture of the first and second knot rows 114a, 114b indicate to a user that the first and second knot rows 114a, 114b have different rates of deployment. In any of these instances, additional rows of the constraint 102 may each include differing strand characteristics such as color, markings, and/or texture. In this manner, and due to the rows having different rates of deployment, a user may select a rate of removal of the constrain 102. For example, the multiple knot rows are configured disrupt in response to a user selection of one of the multiple rows to allow the user to select a rate of constraint removal. In certain instances, the multiple rows are configured to unravel in a set order to define a rate of constraint removal. Potential materials for interlocking strands discussed herein include, for example, polytetrafluoroethylene (PTFE), expanded polytetrafluoroethylene (ePTFE), polyester, polyurethane, fluoropolymers, such as perfluoroelastomers and the like, polytetrafluoroethylene, silicones, urethanes, ultra-high molecular weight polyethylene, aramid fibers, and combinations thereof. Other embodiments for interlocking strands can include high strength polymer fibers such as ultra-high molecular weight polyethylene fibers (e.g., Spectra®, Dyneema Purity®, etc.) or aramid fibers (e.g., Technora®, etc.). Generally, any of the foregoing properties may be assessed using ASTM or other recognized measurement techniques and standards, as would be appreciated by a person of ordinary skill in the field.

FIG. 6 is a side view of a delivery system including the device 104 and the constraint 102, in accordance with an embodiment. In some instances, the interlocking strands (e.g., the first interlocking strand 110 and second interlocking strand 112, for example) are configured to lessen ramping of the device 104 prior to being released. For example, the interlocking strands may lessen ramping of the device 104 prior to the knots of the knot row 114 being released in sequence. As shown in FIG. 6, the device 104 begins to expand to a larger diameter after release of the constraining mechanism 102. The device 104 may have an angle A between the portions held by the constraining mechanism 102 and portions that have been expanded or are beginning to expand. Due to the angle A and the device 104 expending a force to deploy to the deployed diameter D2, prior devices may shift due to ramping of the device 104. The interlocking strands, however, lessen ramping of the device 104 by maintaining a location of each of the knots, relative to the device 104, as the knots of the knot row 114 are released in sequence, lessening undesired or pre-deployment of the device 104 as shown in FIG. 6.

FIG. 6A is an image of a delivery system 10 in a delivery configuration, in accordance with an embodiment. FIG. 6B is an image of a delivery system 10 in a semi-deployed configuration, in accordance with an embodiment. As shown, disrupting one of the interlocking strands (e.g., the first interlocking strand 110, for example) of the first knot row 114a initiates unravelling of at least a portion of the constraint 102 at a first deployment rate, as shown in FIG. 6B. Disrupting one of the interlocking strands of the second knot row 114b (not shown in FIGS. 6A and 6B) initiates unravelling of another portion of the constraint 102 at a second deployment rate. In instances where the constraint 102 includes more than two knot rows, disrupting a strand of consecutive knot rows (e.g., a third knot row 114c and/or a fourth knot row 114d) initiates unravel of another portion of the constraint 102 at another deployment rate (e.g., a third deployment rate or a fourth deployment rate) that may be either different or the same as the first and/or second deployment rates. In other instances, disrupting of one of the rows 114 may independently release the constraint 102 and the user may alter the deployment ratio based on the selection of the knot rows 114.

Figure 7B:
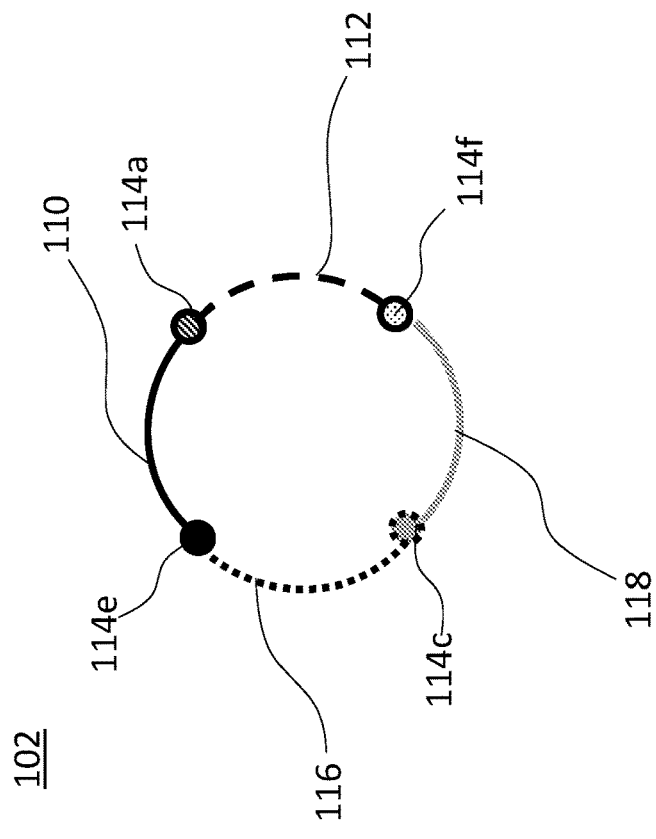
FIG. 7B is an end view of the constraint, shown in FIG. 7A, having an example second knot row pattern, in accordance with an embodiment
Figure 7A:
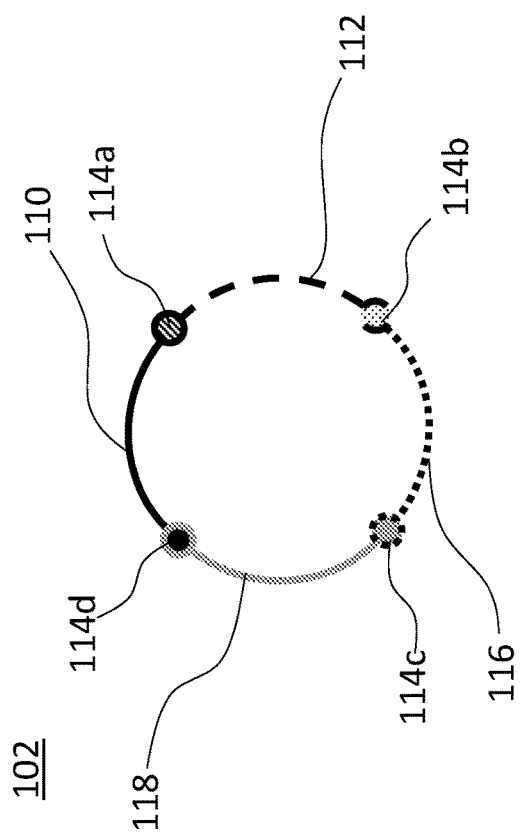
FIG. 7A is an end view of a constraint having an example first knot row pattern, in accordance with an embodiment.

FIG. 7A is an end view of a constraint 102 having an example first knot row pattern, in accordance with an embodiment. The constraint 102 includes a different pattern formed by a plurality of interlocking strands 110, 112, 116, 118 along a length of the constraint. As described in further detail below, the pattern differs based on an interaction between the interlocking strands 110, 112, 116, 118 along the length of the constraint 102.

In some instances, each respective interlocking strand and knot row are configured to unravel selectively by the user. For example, as shown, when one of the interlocking strands (e.g., the first interlocking strand 110, for example) of the first knot row 114a is disrupted, the first knot row 114a unravels at the first deployment rate and a portion of the constraint 102 is released. After initiating unravel of the first knot row 114a, one of the interlocking strands of the second knot row 114b (e.g., the second interlocking strand 112, for example) may be disrupted by the user, thus initiating unravel of the second knot row 114b at the second deployment rate and release of another portion of the constraint 102. After initiating unravel of the second knot row 114b, one of the interlocking strands of the third knot row 114c (e.g., the third interlocking strand 116, for example) may be disrupted by the user, thus initiating unravel of the third knot row 114c at the third deployment rate and release of another portion of the constraint 102. After initiating unravel of the third knot row 114c, one of the interlocking strands of the fourth knot row (e.g., the fourth interlocking strand 118, for example) may be disrupted by the user, thus initiating unravel of the fourth knot row 114d at a fourth deployment rate and release of another portion of the constraint 102. This release method can continue for consecutive knot rows until the constraint 102 is fully released. In other instances, disrupting of one of the rows 114 may independently release the constraint 102 and the user may alter the deployment ratio based on the selection of the knot rows 114.

In various instances, the user can actively select which knot row 114 to deploy at certain times. For example, the knot rows 114 do not have to be deployed consecutively around the circumference of the device 104. For example, the first knot row 114a could be deployed first, followed by the third or fourth knot rows 114c, 114d. Since each of the knot rows 114 can have a different deployment characteristic (e.g., deployment rate, deployment ratio), the user can deliberately deploy knot rows 114 that will provide the deployment characteristics desired during a procedure. In other instances, as is shown in FIG. 7B, the constraint 102 may be formed, woven, or knit, to have multiple knot row patterns along a length of the constraint.

FIG. 7B is an end view of the constraint 102, shown in FIG. 7A, having an example second knot row pattern, in accordance with an embodiment. As shown in FIG. 7B, the locations of the third interlocking strand 116 and the fourth interlocking strand 118 are swapped relative to a circumference of the constraint 102.

Changing the position of the third interlocking strand 116 and the fourth interlocking strand 118 also forms different knot rows 114e, 114f in place of knot rows 114c, 114d. In certain instances, the third interlocking strand 116 and the fourth interlocking strand 118 are altered at some point along a length of the constraint 102 to alter or change the deployment ratio. The interaction between the third interlocking strand 116 and the first interlocking strand 110 may be different than the interaction between the fourth interlocking strand 118 and the first interlocking strand 110. Similarly, the interaction between the fourth interlocking strand 118 and the second interlocking strand 112 may be different than the interaction between the third interlocking strand 116 and the second interlocking strand 112.

Locations of the interlocking strands 110, 112, 116, 118 may be switched to create a constraint 102 that has deployment ratios that differ within the knot rows 114, and can be additionally different along a length of the constraint 102. As a result, a user disrupting one of the knot rows 114 may passively alter deployment while continuing to disrupt the same one of the knot row 114 due to the altered strand locations and altered interactions between the strands. For example, if a user is deploying down knot row 114d is configured to include a first deployment force, but a different deployment force is desired after a certain length of deployment, the position of the third interlocking strand 116 and the fourth interlocking strand 118 may be changed at that location to replace knot row 114d with knot row 114e, which can be configured to include a different (e.g., higher or lower deployment force). Similarly, the interlocking strands 110, 112, 116, 118 merged or split as described below with reference to FIGS. 8A-B.

FIG. 8A is an end view of a constraint 102 having an example first knot row pattern, in accordance with an embodiment. The constraint 102 includes a different pattern formed by a plurality of interlocking strands 110, 112, 116 along a length of the constraint. As described in further detail below, the pattern differs based on an increase or decrease in knot rows 114 along the length of the constraint 102.

In some instances, each respective interlocking strand and knot row are configured to unravel selectively by the user. For example, as shown, when one of the interlocking strands (e.g., the first interlocking strand 110, for example) of the first knot row 114a is disrupted, the first knot row 114a unravels at the first deployment rate and a portion of the constraint 102 is released. After initiating unravel of the first knot row 114a, one of the interlocking strands of the second knot row 114b (e.g., the second interlocking strand 112, for example) may be disrupted by the user, thus initiating unravel of the second knot row 114b at the second deployment rate and release of another portion of the constraint 102. After initiating unravel of the second knot row 114b, one of the interlocking strands of the third knot row 114c (e.g., the third interlocking strand 116, for example) may be disrupted by the user, thus initiating unravel of the third knot row 114c at the third deployment rate and release of another portion of the constraint 102. This release method can continue for consecutive knot rows until the constraint 102 is fully released. In other instances, disrupting of one of the rows 114 may independently release the constraint 102 and the user may alter the deployment ratio based on the selection of the knot rows 114.

In various instances, the user can actively select which knot row 114 to deploy at certain times. For example, the knot rows 114 do not have to be deployed consecutively around the circumference of the device 104. Each of the knot rows 114 can have a different deployment characteristic (e.g., deployment rate, deployment ratio), the user can deliberately deploy knot rows 114 that will provide the deployment characteristics desired during a procedure.

The constraint 102 can have deployment ratios that differ within the knot rows 114 along a length of the constraint 102. Rather than switching the locations of the interlocking strands 110, 112, 116, the interlocking strands 110, 112, 116 may be merged to create different interactions between the interlocking strands 112, 116, 118. As shown in FIG. 8B, for example, the second interlocking strand 112 and the third interlocking strand 116 are merged. Merger of the second interlocking strand 112 and the third interlocking strand 116 creates different knot rows and knot patterns. For example, the merger of the second interlocking strand 112 and the third interlocking strand 116 forms two knot rows 114e, 114f rather than there. The merger of the second interlocking strand 112 and the third interlocking strand 116 creates a different interaction within the constraint 102 than the second interlocking strand 112 and the third interlocking strand 116 being alone.

The merger (or oppositely the splitting of strands) of the interlocking strands 110, 112, 116 may create a constraint 102 that has deployment ratios that differ within the knot rows 114, and can be additionally different along a length of the constraint 102. As a result, a user disrupting one of the knot rows 114 may passively alter deployment while continuing to disrupt the same one of the knot row 114 due to the altered strand locations and altered interactions between the strands. For example, if a user is deploying down knot row 114a is configured to include a first deployment force, but a different deployment force is desired after a certain length of deployment, the second interlocking strand 112 and the third interlocking strand 116 may be merger at that location to replace knot row 114a with knot row 114d or knot row 114e, which can be configured to include a different (e.g., higher or lower deployment force). The interlocking strands 110, 112, 116 may be split rather than merged. For example, the constraint 102 may start with the pattern shown in FIG. 8B and transition to the pattern shown in FIG. 8A.

The merger, location change, or splitting of interlocking strands, as discussed above with reference to FIGS. 7-8, may occur using any number of interlocking strands. For example, the interlocking strands 110, 112, 116, 118 may be merged to form two knot rows and opposite two knot rows 114 can become four knot rows 114. In addition, three knot rows 114 can alter a location as described with reference to FIGS. 7A-B.

In certain instances, a knot row 114 may include multiple pairs of strands, or a pair of strands, or a single strand as described in detail above. The multiple strands may be arranged or knit together and subsequently interlocked with another strand or strands to form knot row 114 (e.g., stands 112, 116 interlocked with strand 110 as shown in FIG. 8B). The knot row 114 may include stands arranged as such along an entire length of a constraint 102 or along only a portion of a length as described with reference to FIG. 8B.

The inventive concepts of this application have been described above both generically and with regard to specific embodiments. It will be apparent to those skilled in the art that various modifications and variations can be made in the embodiments without departing from the scope of the disclosure. Thus, it is intended that the embodiments cover the modifications and variations of the inventive concepts provided they come within the scope of the appended claims and their equivalents.

What is claimed is:

1. A medical device deployment apparatus, the apparatus comprising:
   a constraint configured to releasably constrain the medical device and including a plurality of interlocking strands farming a first knot row configured to unravel at a first deployment rate, a second knot row configured to unravel at a second deployment rate that is different from the first deployment rate, and a third knot row spaced from the first and second knot rows;
   wherein disrupting a strand of the first knot row initiates unraveling of at least a portion of the constraint at the first deployment rate, disrupting a strand of the second knot row initiates unravelling of at least a portion of the constraint at the second deployment rate, and disrupting a strand of the third knot row initiates unraveling of at least a portion of the constraint at a third deployment rate that is different that the first and second deployment rates; and
   wherein a deployment ratio between the first knot row and the second knot row is different than a deployment ratio between the second knot row and the third knot row.

2. The apparatus of claim 1, wherein the deployment ratio between the first knot row and the second knot row is 10:1.

3. The apparatus of claim 1, wherein the first, second, and third knot rows are evenly spaced about a circumference of the constraint.

4. The apparatus of claim 1, wherein the first, second, and third knot rows are unevenly spaced about the circumference of the constraint.

5. The apparatus of claim 1, wherein disrupting the first knot row includes breaking a strand of the first knot row, and wherein disrupting the second knot row includes breaking a strand of the second knot row.

6. The apparatus of claim 1, wherein disrupting the first knot row includes altering tension of at least one strand of the first knot row, and wherein disrupting the second knot row includes altering tension of at least one strand of the second knot row.

7. The apparatus of claim 1, wherein the first knot row is configured to disrupt before the second knot row.

8. The apparatus of claim 1, wherein the second deployment rate is faster than the first deployment rate.

9. The apparatus of claim 1, wherein the strands of the first knot row are distinguishable from the strands of the second knot row by color.

10. The apparatus of claim 1, wherein the strands of the first knot row are distinguishable from the strands of the second knot row by marking.

11. The apparatus of claim 1, wherein the strands of the first knot row are distinguishable from the strands of the second knot row by texture.

12. The apparatus of claim 1, wherein the plurality of interlocking strands forms a warp knit pattern.

13. The apparatus of claim 1, wherein a pattern formed by the plurality of interlocking strands differs along a length of the constraint.

14. The medical device deployment apparatus of claim 1, wherein:
the plurality of interlocking strands form of a warp knit having the first, second and third knot rows spaced around a circumference; and
wherein the knot rows are unevenly distributed around the circumference and a rate of removable constraint removal is different depending upon which of the knot rows is disrupted.

15. The apparatus of claim 14, wherein the knot rows are configured to disrupt in response to a user selection of one of the knot rows to allow the user to select a rate of constraint removal.

16. The apparatus of claim 14, wherein the knot rows are configured to unravel in a set order to define a rate of constraint removal.

17. The apparatus of claim 14, wherein the interlocking strands are distinguishable from one another.

18. The apparatus of claim 17, wherein the interlocking strands are distinguishable from one another by coloring.

19. The apparatus of claim 17, wherein the interlocking strands are distinguishable from one another by marking.

20. The apparatus of claim 17, wherein the interlocking strands are distinguishable from one another by texture.

21. A medical device deployment apparatus, the apparatus comprising:
a constraint configured to releasably constrain the medical device and including a plurality of interlocking strands forming a first knot row configured to unravel at a first deployment rate and a second knot row configured to unravel at a second deployment rate that is different from the first deployment rate;
wherein disrupting a strand of the first knot row initiates unraveling of at least a portion of the constraint at the first deployment rate, disrupting a strand of the second knot row initiates unravelling of at least a portion of the constraint at the second deployment rate;
wherein a pattern formed by the plurality of interlocking strands differs along a length of the constraint; and
wherein the plurality of interlocking strands form a plurality of knot rows, including the first knot row and the second knot row, that increases or decreases in number along the length of the constraint.

22. A medical device deployment apparatus, the apparatus comprising:
a constraint configured to releasably constrain the medical device and including a plurality of interlocking strands forming a first knot row configured to unravel at a first deployment rate and a second knot row configured to unravel at a second deployment rate that is different from the first deployment rate;
wherein disrupting a strand of the first knot row initiates unraveling of at least a portion of the constraint at the first deployment rate, disrupting a strand of the second knot row initiates unravelling of at least a portion of the constraint at the second deployment rate;
wherein a pattern formed by the plurality of interlocking strands differs along a length of the constraint; and
wherein the plurality of interlocking strands form a plurality of knot rows, including the first knot row and the second knot row, and interactions between the plurality of interlocking strands differs along the length of the constraint.

23. A method of using a medical device deployment apparatus, the method comprising:
providing a constraint including a first knot row, a second knot row, and a third knot row;
disrupting a strand of the first knot row to initiate unravelling of at least a portion of the constraint at a first deployment rate;
disrupting a strand of the second knot row to initiate unravelling of at least a portion of the constraint at a second deployment rate that is greater than the first deployment rate;
disrupting a strand of the third knot row to initiate unravelling of at least a portion of the constraint at a third deployment rate that is different than the first and second deployment rates; and
wherein a deployment ratio between the first knot row and the second knot row is different than a deployment ratio between the second knot row and the third knot row.

24. The method of claim 23, wherein disrupting the strand of the first knot row includes breaking the strand.

* * * * *